US010413940B2

(12) United States Patent
De Wijs et al.

(10) Patent No.: US 10,413,940 B2
(45) Date of Patent: Sep. 17, 2019

(54) TRANSDUCER LAMINATE

(71) Applicant: KONINKLIJKE PHILIPS N.V., Eindhoven (NL)

(72) Inventors: Willem-Jan Arend De Wijs, Oss (NL); Johannes Wilhelmus Weekamp, Beek en Donk (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/745,764

(22) PCT Filed: Jul. 21, 2016

(86) PCT No.: PCT/EP2016/067450
§ 371 (c)(1),
(2) Date: Jan. 18, 2018

(87) PCT Pub. No.: WO2017/013224
PCT Pub. Date: Jan. 26, 2017

(65) Prior Publication Data
US 2018/0207683 A1    Jul. 26, 2018

(30) Foreign Application Priority Data

Jul. 21, 2015 (EP) .................................. 15177667

(51) Int. Cl.
*B06B 1/06* (2006.01)
*H01L 41/047* (2006.01)
(Continued)

(52) U.S. Cl.
CPC ........ *B06B 1/0688* (2013.01); *A61B 17/3403* (2013.01); *A61M 25/0108* (2013.01);
(Continued)

(58) Field of Classification Search
CPC .............. B06B 1/0688; B06B 2201/56; A61B 17/3403; A61M 25/0108; H01L 41/313; H01L 41/0475
See application file for complete search history.

(56) References Cited

U.S. PATENT DOCUMENTS

| 4,339,683 A | 7/1982 | Scott |
| 5,313,957 A | 5/1994 | Little |

(Continued)

FOREIGN PATENT DOCUMENTS

| DE | 3425882 A1 | 1/1986 |
| EP | 1905479 A1 | 4/2008 |

(Continued)

*Primary Examiner* — Bryan P Gordon (57) ABSTRACT

A transducer laminate in which electrical contact is made between electrical conductors (C1, C2) and a transducer layer (TY). The transducer laminate includes two adhesive-coated foils (F1, F2), whose adhesive coatings (AC1, AC2) are arranged to face each other. At a first position (A-A') along the length of the two electrical conductors (C1, C2) the two electrical conductors (C1, C2) are sandwiched between the adhesive coatings (AC1, AC2) of the two adhesive-coated foils, and the transducer layer (TY) is also sandwiched between the two electrical conductors (C1, C2) such that electrical contact is made with the electrodes (E1, E2) on the transducer layer (TY). At a second position (B-B') along the length of the two electrical conductors (C1, C2) the two electrical conductors (C1, C2) are sandwiched between the adhesive coatings (AC1, AC2) of the two adhesive-coated foils and there is no transducer layer (TY) sandwiched between the two electrical conductors (C1, C2).

21 Claims, 6 Drawing Sheets

(51) Int. Cl.
*H01L 41/29* (2013.01)
*H01L 41/313* (2013.01)
*A61M 25/01* (2006.01)
*A61B 17/34* (2006.01)
*H01L 41/193* (2006.01)

(52) U.S. Cl.
CPC .......... *H01L 41/0475* (2013.01); *H01L 41/29* (2013.01); *H01L 41/313* (2013.01); *A61B 2017/3413* (2013.01); *B06B 2201/56* (2013.01); *B06B 2201/76* (2013.01); *H01L 41/193* (2013.01)

(56) References Cited

U.S. PATENT DOCUMENTS

| | | |
|---|---|---|
| 7,608,047 B2 | 10/2009 | Stasz |
| 8,885,034 B2 | 11/2014 | Adair |
| 2009/0263854 A1* | 10/2009 | Jacono ............ G01N 33/48778 435/29 |
| 2010/0090332 A1* | 4/2010 | Kim ........................ H01C 1/028 257/692 |
| 2011/0297219 A1* | 12/2011 | Vogeli ............... H01L 31/02242 136/256 |
| 2013/0140955 A1* | 6/2013 | Chaggares .......... H01L 41/0475 310/334 |
| 2014/0088389 A1 | 3/2014 | Simpson |
| 2016/0132183 A1 | 5/2016 | Naoi |
| 2017/0172618 A1 | 6/2017 | Erkamp |

FOREIGN PATENT DOCUMENTS

| | | |
|---|---|---|
| JP | 61040071 A | 2/1986 |
| WO | 2010033819 A1 | 3/2010 |
| WO | 2013148149 A1 | 10/2013 |
| WO | 2013177573 A2 | 11/2013 |

\* cited by examiner

FIG. 8B

TRANSDUCER LAMINATE

CROSS-REFERENCE TO PRIOR APPLICATIONS

This application is the U.S. National Phase application under 35 U.S.C. § 371 of International Application No. PCT/EP2016/067450, filed on Jul. 21, 2016, which claims the benefit of European Patent Application No. 15177667.1, filed on Jul. 21, 2015. These applications are hereby incorporated by reference herein.

FIELD OF THE INVENTION

The invention relates to the provision of electrical contact to a transducer and finds application in the transducer field in general. More particularly the transducer may for example be a piezoelectric transducer, such as a piezoelectric ultrasound transducer. Moreover the transducer can be attached to a medical device for use in tracking the position of the device within an ultrasound field.

BACKGROUND OF THE INVENTION

Transducers are used in all fields of industry ranging from portable electronic devices, optics, biotechnology, solar to the medical device field. These transducers, which include for example ultrasound, thermal, capacitive-sensing, impedance-sensing, optical and mechanical, or MEMS devices, enable a vast array of sensing and energy conversion applications. Such transducers are frequently provided in the form of a layer, i.e. a sheet. Sometimes the transducer is made directly from, for example, a layer or sheet of electrically active material, although in other cases the layer may comprise a plurality of sub-layers or strata that together provide the transducer's function. Examples of transducer layers include piezoelectric layers, light emitting layers such as LED and OLED, light sensitive layers such as solar cells, pressure-sensitive layers and capacitive-sensing layers. MEMS transducers used in e.g. motion sensing may also be provided in the form of a layer. Polyvinylidene fluoride, i.e. PVDF, and the related materials in the PVDF group that include PVDF co-polymers and PVDF ter-polymers are examples of electrically active, or even more specifically piezoelectric, materials that are provided in the form of a layer from which transducers can be made directly. Piezoelectric materials are used in some of the above applications since they are responsive to pressure, and vice-versa, contract or expand when an electrical field is applied. All these applications, however suffer from the need to make electrical contact with the transducer layer in order to convey electrical signals to and from the transducer.

One example of the above need arises in the medical device field as described in currently unpublished PCT application PCT/IB2015/052425. In this it is required to make electrical contact with a piezoelectric sensor that is ultimately attached to a medical device. In this example the piezoelectric sensor is responsive to ultrasound signals which are used to track the position of the medical device within an ultrasound field. This need to make electrical contact with a transducer may be aggravated by the need to attach the transducer to the curved surface of a medical device, such as the shaft of a catheter or needle, and to convey electrical signals thereto.

Electrical solders present an obvious solution to this need, but the thermal constraints imposed by the transducer itself often demand the use of more costly low-temperature solders. A range of conductive adhesives have also been developed for this purpose.

Patent application WO2013/148149A1 relates to photovoltaic modules and discloses a means for making electrical contact with photovoltaic cells. In some embodiments a pressure sensitive adhesive, i.e. PSA, is used to facilitate such contact with one side of the solar cell. Patent application US2011/0297219A1 also relates to photovoltaic devices and also discloses the use of a pressure sensitive adhesive for making electrical contact with one side of photovoltaic devices.

Document US2010/0090332A1 describes a ceramic chip assembly that includes a ceramic base, a plurality of external electrodes, a pair of cylindrical metal lead wires, and an insulating protection material. The pair of external electrodes is oppositely formed on both side surfaces of the ceramic base, respectively. The cylindrical metal lead wire has one end thereof electrically and mechanically connected to the external electrodes by an electrical conductive adhesive, respectively, and has an external diameter identical to or greater than the thickness of the ceramic base. The insulating protection material includes a pair of insulating films and an insulating coating layer.

Document JP61040071 describes a high-polymer piezoelectric member that has thin-film electrodes. A flexible electrode sheet includes a high-polymer film, a thin-film lead part connected to an electrode, and another electrode having a lead part connected to yet another electrode. One of the electrodes is attached to a piezoelectric member and is bonded to another of the electrodes by an electrically conductive adhesive. Some of the electrodes are connected together by bonding an electrically conductive adhesive-backed copper foil between them.

The present invention seeks to address drawbacks of the above and other known solutions to this and related problems.

SUMMARY OF THE INVENTION

It is an object of the present invention to provide electrical contact to a transducer. Thereto an apparatus, a method of assembling the apparatus, and a method of attaching the apparatus to an elongate device are provided as defined in the independent claims.

In accordance with one aspect of the invention a transducer laminate is provided. The transducer laminate includes two adhesive-coated foils F1, F2, whose adhesive coatings AC1, AC2 are arranged to face each other. At a first position A-A' along the length of two electrical conductors C1, C2 the two electrical conductors C1, C2 are sandwiched between the adhesive coatings AC1, AC2 of the two adhesive-coated foils, and the transducer layer TY is also sandwiched between the two electrical conductors C1, C2 such that electrical contact is made with the electrodes E1, E2 on the transducer layer TY. At a second position B-B' along the length of the two electrical conductors C1, C2 the two electrical conductors C1, C2 are sandwiched between the adhesive coatings AC1, AC2 of the two adhesive-coated foils and there is no transducer layer TY sandwiched between the two electrical conductors C1, C2. Thereby, a transducer laminate that includes an electrical bus is provided.

In accordance with another aspect of the invention there is a gap DS between the centers of the two electrical conductors C1, C2 in a plane parallel to the transducer layer.

In accordance with another aspect of the invention each of the two electrical conductors C1, C2 comprises a wire having a substantially circular cross section.

In accordance with another aspect of the invention each wire has a diameter DW; and the ratio of the gap between the centers of the two electrical conductors to the wire diameter DS/DW is greater than or equal to 10.

In accordance with another aspect of the invention each foil in the transducer laminate is formed from one of the following materials: Polyvinylidene fluoride, a PVDF copolymer such as polyvinylidene fluoride trifluoroethylene, a PVDF ter-polymer such as P(VDF-TrFE-CTFE).

In accordance with another aspect of the invention at least one of the two adhesive-coated foils F1, F2 of the transducer laminate TL is further provided with one or more openings for making electrical contact to at least a portion of each of the two electrical conductors C1, C2.

In accordance with another aspect of the invention i) at least one of the foils is provided by a conductive material, and/or ii) at least one of the foils (F1, F2) comprises a conductive layer (CL) that extends substantially along the length of the two electrical conductors (C1, C2).

In accordance with another aspect of the invention one of the two adhesive-coated foils F1, F2 further comprises a second adhesive coating AC3 on the other of its two surfaces.

In accordance with another aspect of the invention at least one of the adhesive coatings AC1, AC2, AC3 is a pressure sensitive adhesive coating.

In accordance with another aspect of the invention the transducer is an ultrasound transducer that is capable of emitting and/or detecting ultrasound signals.

DETAILED DESCRIPTION OF THE INVENTION

As described above, the present invention provides electrical connection to a transducer. Thereto, a transducer laminate is provided.

Figure 1A:
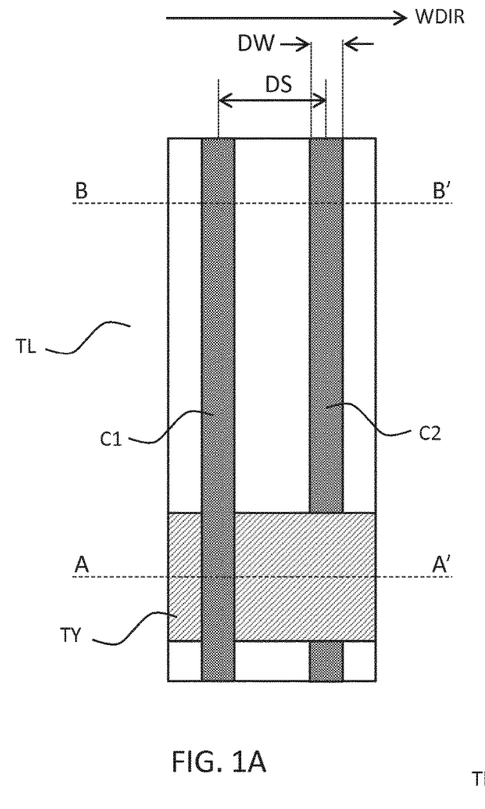
FIGS. 1A-1E illustrate a transducer laminate TL in accordance with some aspects of the invention, in planar view in FIG. 1A, along section B-B' in FIG. 1B, along section A-A' in FIG. 1C, along section B-B' in expanded view prior to sandwiching in FIG. 1D, and along section A-A' in expanded view prior to sandwiching in FIG. 1E.
Figure 1B:
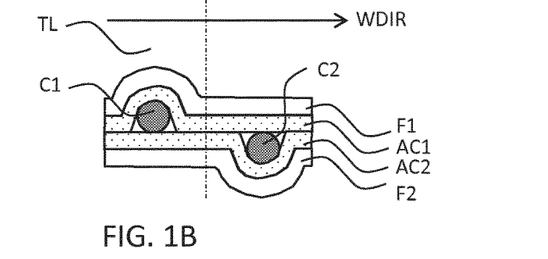
Figure 1C:
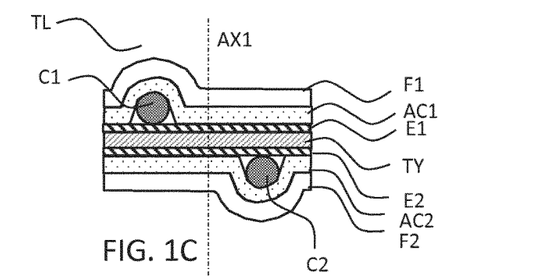
Figure 1D:
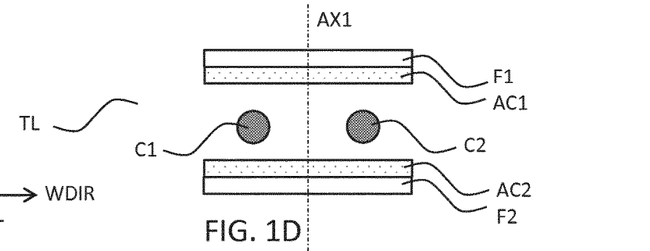
Figure 1E:
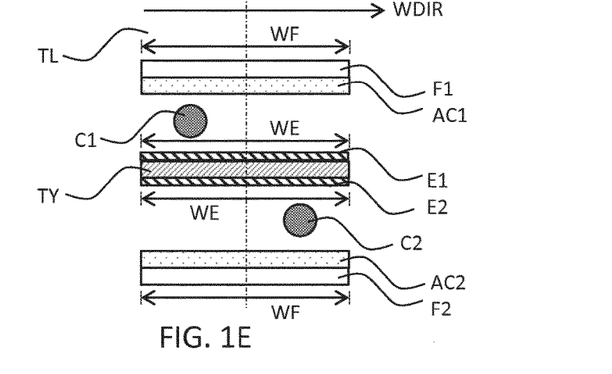

FIGS. 1A-1E illustrate a transducer laminate TL in accordance with some aspects of the invention, in planar view in FIG. 1A, along section B-B' in FIG. 1B, along section A-A' in FIG. 1C, along section B-B' in expanded view prior to sandwiching in FIG. 1D, and along section A-A' in expanded view prior to sandwiching in FIG. 1E. The transducer laminate in FIGS. 1A-1E includes two adhesive-coated foils F1, F2, two electrical conductors C1, C2, and a transducer layer TY. Each foil F1, F2 has an adhesive coating AC1, AC2 on one of its two surfaces, and as shown in, e.g., FIG. 1E, each foil F1, F2 has a foil lateral width WF in a transducer laminate width direction WDIR. The two electrical conductors C1, C2 are arranged alongside each other and extend along a common direction. The transducer layer TY has an electrode E1, E2 on each of its two surfaces, and as shown in, e.g., FIG. 1E, each electrode E1, E2 has an electrode lateral width WE in the transducer laminate width direction WDIR. A minimum separation between the two electrodes (E1, E2) may define a transducer axis AX1. The foils may be formed from a range of polymer materials, for example Polyethylene terephthalate (PET), Polyimides (PI), or Polyamides (PA). Preferably the foils are formed from an electrically insulating material. The adhesive coatings AC1, AC2 may in principle be any adhesive coating, although a pressure sensitive adhesive, i.e. PSA, coating is preferred. Pressure sensitive adhesives are a class of materials that form an adhesive bond upon application of pressure. Advantageously, pressure sensitive adhesives provide a reliable bond and thereby a robust structure that is quick to assemble. Suitable pressure sensitive adhesives include product 2811CL made by the 3M corporation. These may be supplied as PSA-coated polymer sheets such as product 9019 supplied by the 3M corporation. PSA-coated polymer sheets are typically provided with a removable outer layer that is peeled away to reveal the adhesive coating and thereby protect the adhesive layer until its adhesive properties are required. Moreover the adhesive coatings AC1, AC2 are preferably formed from an electrically insulating material. The electrical conductors C1, C2 provide electrical contact with corresponding electrodes E1, E2 on the surfaces of the transducer layer, thereby providing an electrical bus that connects to the transducer. Suitable electrical conductor materials include metals, for example, gold, aluminum, copper, silver and chrome. Preferably the electrical conductors are in the form of a wire. Advantageously the use of wires, which conventionally have a substantially circular cross section, improves the flexibility of the so-produced transducer laminate. Such wires are more resilient against bending in different directions as compared to the use of electrically conductive strips, or tracks which conventionally have a more rectangular cross section. Thus, the use of wires is particularly beneficial when attaching the transducer layer to a non-planar surface.

The transducer layer TL may in principle be any type of transducer that is available in the form of a layer; i.e. a shape having two major surfaces. The transducer may provide a sensing function or an actuation function. The layer may comprise a plurality of sub-layers, or strata that together provide the transducer's function. Examples of transducer layers include piezoelectric layers, light emitting layers such as LED and OLED, light sensitive layers such as solar cells, pressure-sensitive layers and capacitive-sensing layers. MEMS transducers used in e.g. motion sensing may also be provided in the form of a layer. Preferably the transducer layer TL is a piezoelectric transducer layer, and more specifically is a piezoelectric ultrasound transducer layer that may for example be formed from Polyvinylidene fluoride, i.e. PVDF, or the related materials in the PVDF group including PVDF co-polymers such as polyvinylidene fluoride trifluoroethylene, and PVDF ter-polymers such as P(VDF-TrFE-CTFE). These materials are available in the form of a flexible layer and can provide a piezoelectric transducer suitable for attaching to a non-planar surface. The invention is however not limited to these specific examples.

Returning to the transducer laminate TL of FIGS. 1A-1E, the adhesive coatings AC1, AC2 of the two adhesive-coated foils F1, F2 are arranged to face each other. Moreover, at a first position, indicated by section A-A', along the length of the two electrical conductors C1, C2 the two electrical conductors C1, C2 are sandwiched between the adhesive coatings AC1, AC2 of the two adhesive-coated foils, and the transducer layer TY is also sandwiched between the two electrical conductors C1, C2 such that one of the two electrical conductors makes electrical contact with one of the two electrodes E1, E2 of the transducer layer TY, and such that the other of the two electrical conductors C1, C2 makes electrical contact with the other of the two electrodes E1, E2 of the transducer layer TY. As illustrated in FIGS. 1A-1E, the two adhesive-coated foils F1, F2 are preferably arranged layer-wise along the transducer axis AX1 such that one of the two adhesive-coated foils F1, F2 is on one side of the transducer layer TY and the other of the two adhesive-coated foils F1, F2 is on the other side of the transducer layer TY. At a second position, indicated by section B-B', along the length of the two electrical conductors C1, C2 the two electrical conductors C1, C2 are sandwiched between the adhesive coatings AC1, AC2 of the two adhesive-coated foils and there is no transducer layer TY sandwiched between the two electrical conductors C1, C2. The first position, i.e. at A-A' may for example correspond to an end of the transducer laminate, such as the distal end of the transducer laminate. Alternatively the transducer layer TY may be arranged for example in the middle, or at any position along the length of the transducer laminate. Electrical connection may be provided at both ends of the transducer laminate. Moreover it is also contemplated to arrange multiple transducer layers TY along the length of the two electrical conductors C1, C2 in order to provide electrical contact with a plurality of such transducer layers TY.

In so doing, electrical contact to the transducer layer TY is provided in the transducer laminate TL at the first position along the length of the electrical conductors, i.e. at A-A', by the electrical conductors C1, C2 which are sandwiched, i.e. held, against corresponding electrodes E1, E2 by the adhesive coatings AC1, AC2, of the foils F1, F2. At the second position along the length of the electrical conductors, i.e. at B-B', which has no transducer laminate, an electrical bus is provided for connecting with the transducer layer, or layers TY. Desirably the extent of the second portion, i.e. B-B', along the length of the electrical conductors exceeds the extent of the first portion, i.e. A-A' along the length of the electrical conductors. Thus a useful length of electrical bus is provided. Preferably the ratio of these two extents is greater than or equal to 5, or greater than or equal to 10, or greater than or equal to 50, or greater than or equal to 100. The electrical bus may be used to electrically connect the transducer with for example a separate electrical or signal processing circuit. Advantageously the combined electrical bus and transducer is contained within the two foils F1, F2. These provide a smooth outer surface that protects against contamination or degradation of the transducer or its electrical conductors. This is particularly advantageous for example in medical applications because it provides a continuous barrier between the transducer materials and the environment. Moreover this permits the testing of the transducer when it is in a sealed environment that corresponds closely with the environment in which it is ultimately used, thereby minimizing differences between its performance when tested and when in-use. Furthermore, reliable electrical contact with the transducer layer is provided by the described transducer laminate in a thin, flexible form factor.

Figure 2:
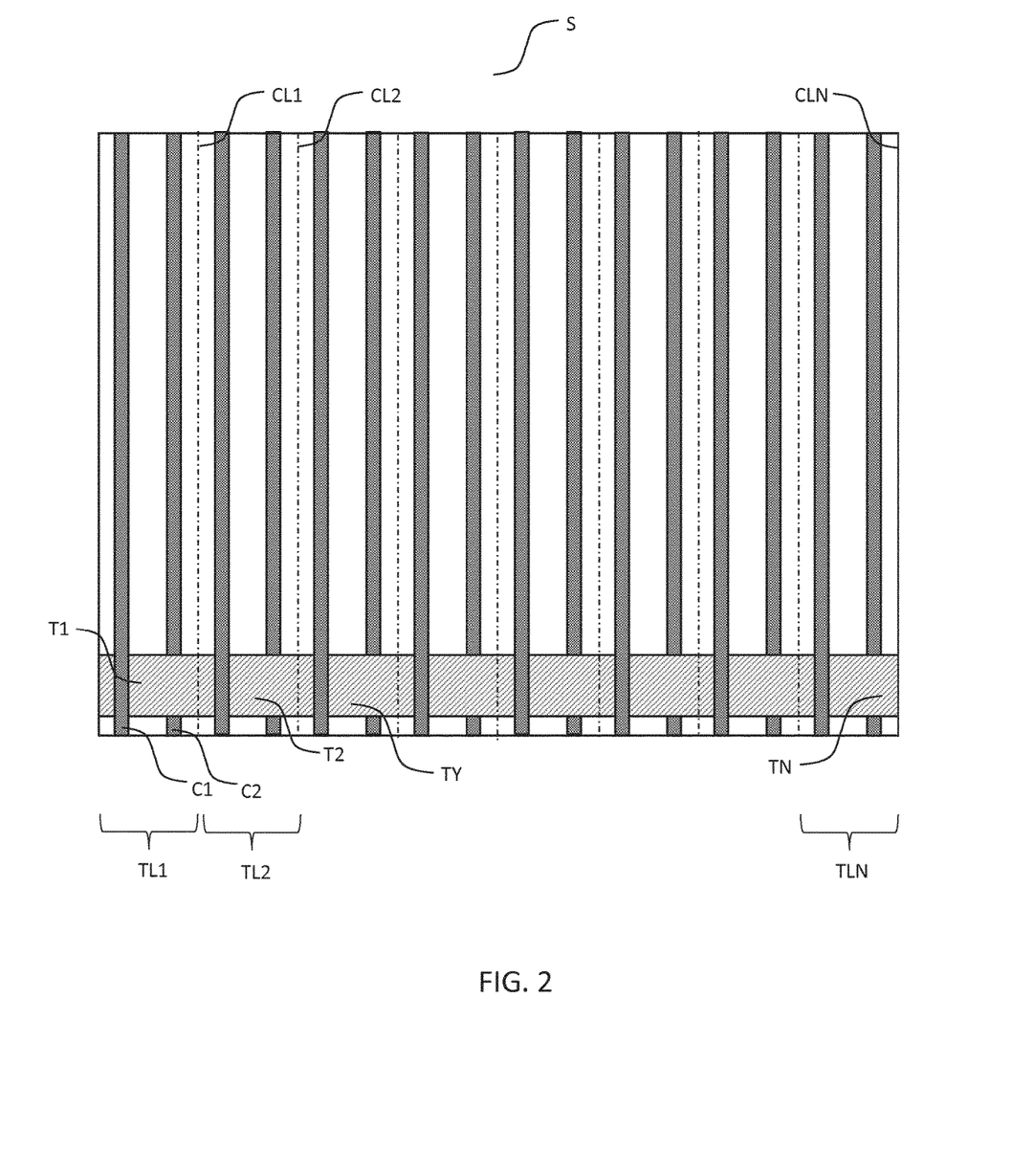
FIG. 2 illustrates a substrate S comprising an array of transducer laminates TL1, TL2, TLN, separable along cutting lines CL1, CL2, CLN, that provide electrical contact with corresponding individual transducers T1, T2, TN.

FIG. 2 illustrates a substrate S comprising an array of transducer laminates TL1, TL2, TLN, separable along cutting lines CL1, CL2, CLN, that provide electrical contact with corresponding individual transducers T1, T2, TN. Thus, the transducer laminate of FIG. 1 is relatively simple to manufacture because a substrate having an array of such transducer laminates can be rapidly manufactured by for example providing transducer layer TY as a continuous strip running transverse to the direction of the electrical conductors and sandwiching this between alternate wires. Subsequently individual transducer laminates may be released from the substrate, for example by a cutting process as indicated by the cut lines CL1, CL2, CLN in FIGS. 1A-1E.

In a further embodiment, not illustrated, at least one of the two adhesive-coated foils F1, F2 of the transducer laminate TL is further provided with one or more openings for making electrical contact to at least a portion of each of the two electrical conductors C1, C2. The opening, or openings, are preferably at the second position along the length of the two electrical conductors C1, C2; i.e. along a portion of the electrical bus. Moreover the opening or openings are desirably coincident with the electrical wires. Thus a single common opening that exposes a portion of each electrical conductor C1, C2 may be used, or more than one opening may be used. Moreover the openings may both be on one side of the transducer layer, for example by making openings in either F1 or F2, or there may be openings on both sides of the transducer layer, for example by making an opening in each of F1 and F2 for providing electrical contact from one or both sides. The opening(s) may thus be used to provide electrical contact to an external electrical circuit. The opening(s) can be made by for example cutting an opening in the form of a window in one of the foils F1, F2 and locally removing a portion of the adhesive layer AC1, AC2 after assembly of the transducer laminate. Alternatively such an opening may be formed a foil F1, F2 prior to the assembly of the transducer laminate with the benefit that the adhesive layer is removed together with the portion of foil to which it is attached.

Figure 3A:
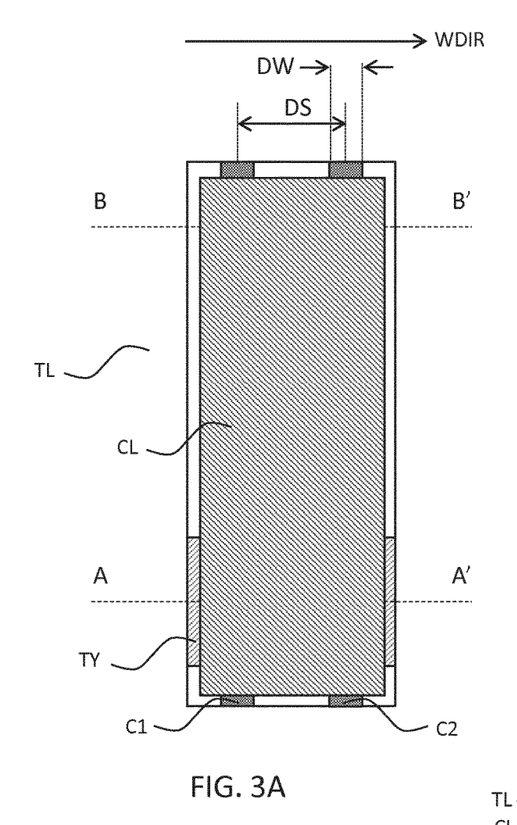
FIGS. 3A-3E illustrate a transducer laminate TL in which foil F1 further includes a conductive layer CL that extends substantially along the length of the two electrical conductors C1, C2, in planar view in FIG. 3A, along section B-B' in FIG. 3B, along section A-A' in FIG. 3C, along section B-B' in expanded view prior to sandwiching in FIG. 3D, and along section A-A' in expanded view prior to sandwiching in FIG. 3E.
Figure 3B:
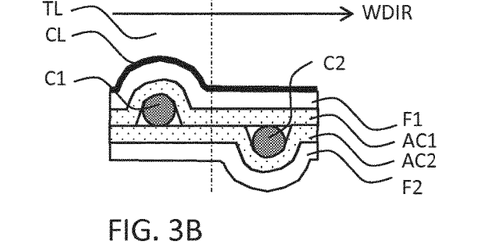
Figure 3C:
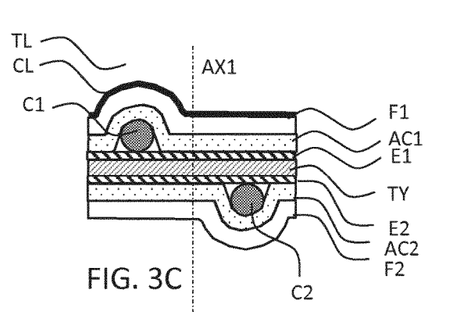
Figure 3D:
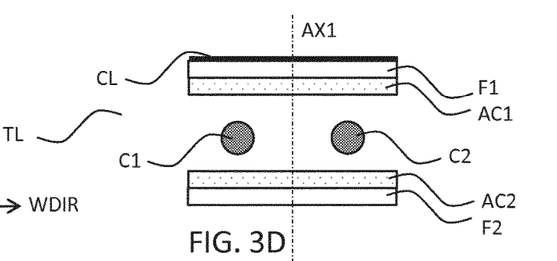
Figure 3E:
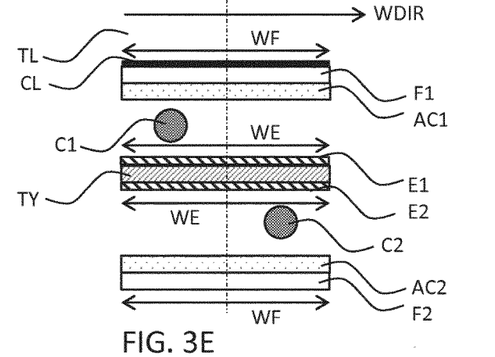

FIGS. 3A-3E illustrate a transducer laminate TL in which foil F1 further includes a conductive layer CL that extends substantially along the length of the two electrical conductors C1, C2, in planar view in FIG. 3A, along section B-B' in FIG. 3B, along section A-A' in FIG. 3C, along section B-B' in expanded view prior to sandwiching in FIG. 3D, and along section A-A' in expanded view prior to sandwiching in FIG. 3E. The conductive layer provides an electrical screen which acts to electrically shield the electrical conductors C1, C2. Preferably the conductive layer furthermore extends across at least the combined width of the two electrical conductors in order to optimize the electrical screening. Advantageously the signal to noise ratio of signals detected by the transducer at the ends of the electrical conductors is thereby improved because the conductive layer shields against interference which may be picked-up by the electrical conductors. In a corresponding manner, when the electrical conductors are used to convey electrical signals to the transmitter, the conductive layer CL reduces electrical interference between the conductors and nearby electrical systems. As alternatives to the embodiment of FIGS. 3A-3E, either or both foils F1 or F2 may include such a conductive layer. It is also contemplated that instead of using an additional layer to provide the electrical screen as described above, at least one of the foils is provided by a conductive material. Thus, rather than use a polymer material for the foils F1, F1, one or both of these foils may be provided by a(n) electrically conductive layer(s). In this implementation, electrical insulation between the electrically conductive foil and the electrical conductors C1, C2 is provided by the adhesive coatings AC1, AC2. This latter implementation removes the need for additional layers in the transducer laminate.

Figure 4A:
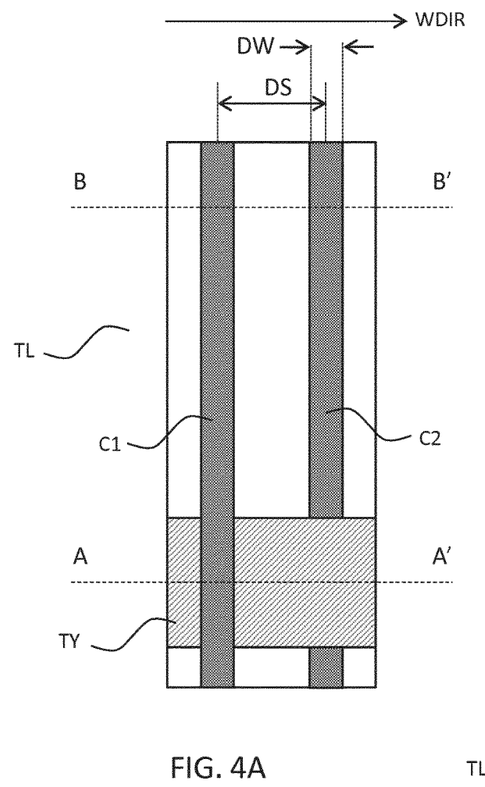
FIGS. 4A-4E illustrate a transducer laminate TL which foil F2 further includes a second adhesive coating AC3 on the other of its two surfaces, in planar view in FIG. 4A, along section B-B' in FIG. 4B, along section A-A' in FIG. 4C, along section B-B' in expanded view prior to sandwiching in FIG. 4D, and along section A-A' in expanded view prior to sandwiching in FIG. 4E.
Figure 4B:
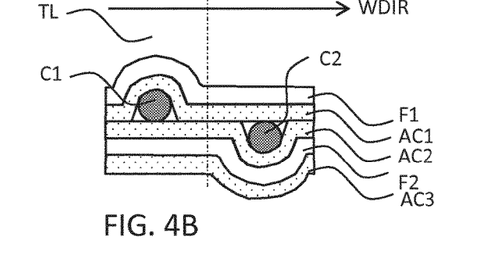
Figure 4C:
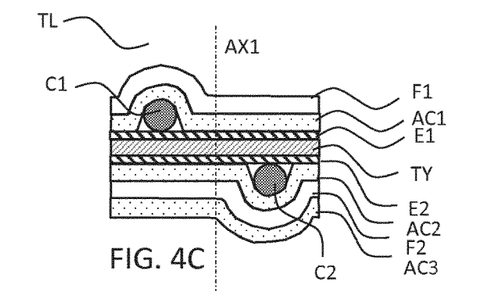
Figure 4D:
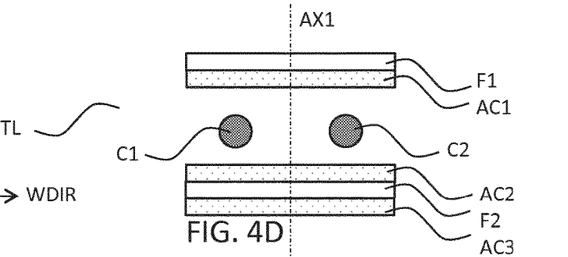
Figure 4E:
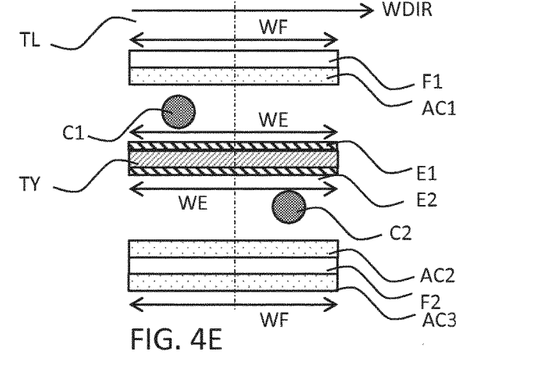

FIGS. 4A-4E illustrate a transducer laminate TL which foil F2 further includes a second adhesive coating AC3 on the other of its two surfaces, in planar view in FIG. 4A, along section B-B' in FIG. 4B, along section A-A' in FIG. 4C, along section B-B' in expanded view prior to sandwiching in FIG. 4D, and along section A-A' in expanded view prior to sandwiching in FIG. 4E. Thus both surfaces of that foil include adhesive coatings. In so doing, the second foil F2 can be easily attached to a device, such as a medical needle, by means of the second adhesive coating AC3. In other words the second adhesive coating AC3 is suitable for attaching the transducer laminate TL to a device. Preferably the second adhesive coating AC3, as with adhesive coating AC2 on foil F2, is formed from a pressure sensitive adhesive as described above. In so doing the transducer laminate can be easily attached to the device simply through application of pressure. Preferably the adhesive coating AC3 is formed from an electrically insulating material.

In each of the embodiments illustrated in FIGS. 1A-1E, 2, 3A-3E and 4A-4E, the two electrical conductors C1, C2 in the transducer laminate TL are illustrated as being laterally displaced with respect to the transducer layer TY such that there is a gap DS between the centers of the two electrical conductors C1, C2 in a plane parallel to the transducer layer. The gap DS acts to reduce the capacitance between the two electrical conductors C1, C2 which might otherwise affect the high frequency electrical performance of transducer TY. Such capacitance can in combination with parasitic resistance and inductance of the electrical wires and transducer, act as a filter which limits the sensitivity of the transducer to high frequency signals. This is particularly important in ultrasound applications. Moreover the gap also acts to reduce the thickness of the transducer layer in a direction perpendicular to the transducer layer. This is particularly advantageous in applications where it is desired to attach the transducer layer to a medical device, such as a medical needle, where any additional thickness affects the penetration capability of the needle. If the electrical conductors were instead arranged on top of one another this effect would not be achieved because a much thicker transducer laminate would be provided. It is noted that in practice when the transducer layer of, e.g., FIGS. 1A-1E, is attached to a planar surface the structure would slightly twist, thereby providing the desired reduction in topography.

In each of the embodiments illustrated in FIGS. 1A-1E, 2, 3A-3E and 4A-4E, preferably each of the two electrical conductors C1, C2 are formed from, or comprise, a wire having a substantially circular cross section. As described above, this improves the flexibility of the transducer laminate. Preferably, if each wire has a diameter defined by DW, and the gap between the wires as defined above is DS, then the ratio DS/DW is greater than or equal to 10, or greater than or equal to 20 or greater than or equal to 100. Increasing the ratio DS/DW acts to further reduce the capacitance between the wires, and thus its impact on the high frequency performance of the transducer.

The embodiments of FIGS. 1A-1E, 2, 3A-3E and 4A-4E, may be assembled through the method steps defined in the independent claims. The sandwiching process ensures that the various components of the transducer laminate are held in-place by means of the adhesive layer. Preferably the adhesive layer is a pressure sensitive adhesive layer as described above, and thus the sandwiching process involves the application of pressure in a perpendicular direction to the transducer layer.

In all the embodiments described herein, typical thickness dimensions of the various layers are as follows: foil 1-50 microns; adhesive layer 5-50 microns; removable outer layer 4-35 microns; however it should be appreciated that these dimensions are purely illustrative and the invention is not limited to these examples.

Figure 5:
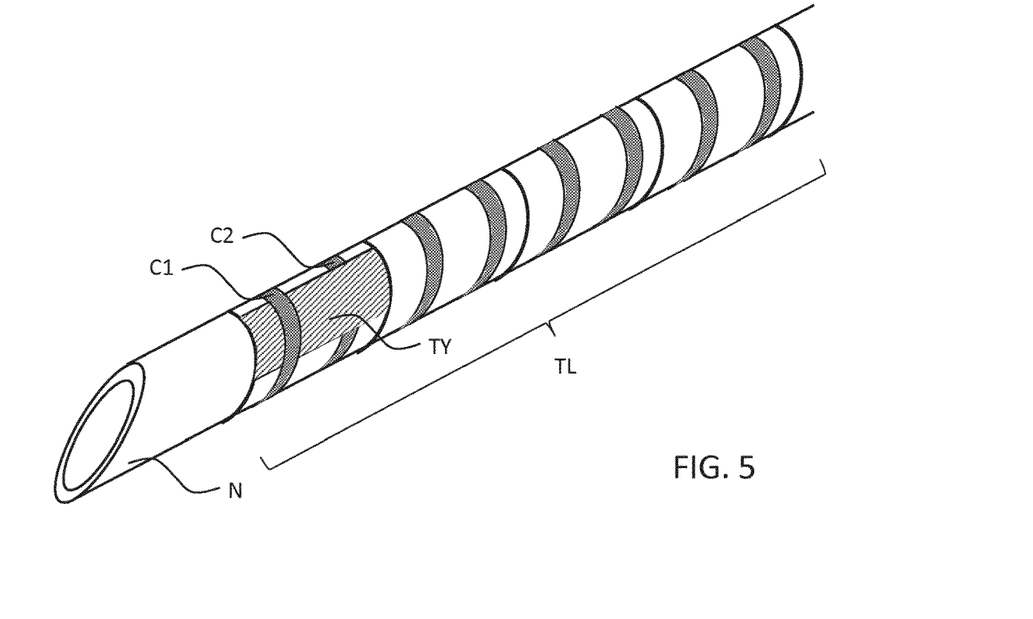
FIG. 5 illustrates an elongate device N in which transducer laminate TL is attached thereto by means of a second adhesive coating AC3 and by wrapping the transducer laminate TL around the elongate device N in the form of a spiral.

The transducer laminate may subsequently be attached to an article. The article may be medical device, or more specifically an elongate device such as a medical cannula or needle. Advantageously the so-described transducer laminate has a thin form factor making it particularly suited for attachment to the shaft of such a medical cannula or needle without affecting its penetration characteristics. Preferably the attachment to the article is made using the second adhesive coating AC3 described in relation to FIGS. 4A-4E. FIG. 5 illustrates an elongate device N in which transducer laminate TL is attached thereto by means of a second adhesive coating AC3 and by wrapping the transducer laminate TL around the elongate device N in the form of a spiral. The wrapping process may for example be achieved by rolling the elongate device N across the second adhesive coating AC3.

Figure 6:
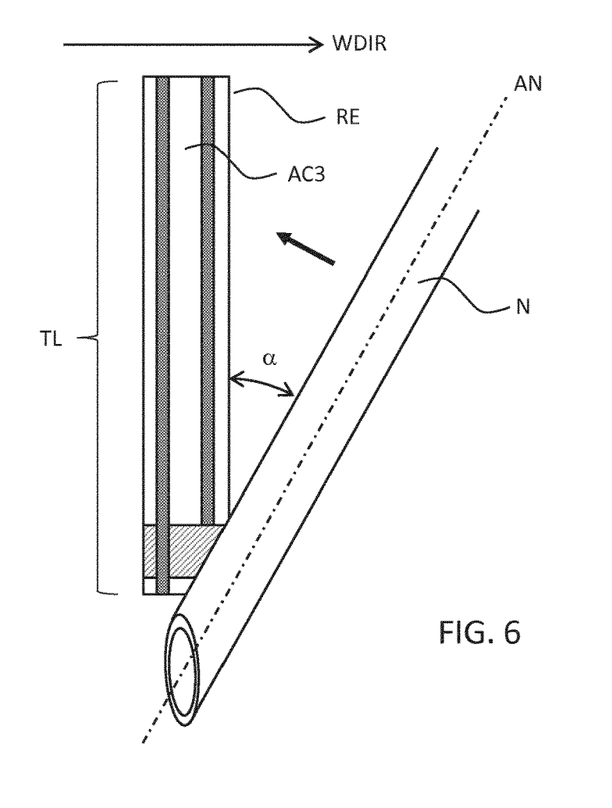
FIG. 6 illustrates a method of attaching a transducer laminate TL to an elongate device N, such as a medial needle, by means of a second adhesive coating AC3 on the surface of the transducer laminate and by rolling the elongate device N across the second adhesive coating AC3 in the direction of the arrow.

FIG. 6 illustrates a method of attaching a transducer laminate TL to an elongate device N, such as a medial needle, by means of a second adhesive coating AC3 on the surface of the transducer laminate and by rolling the elongate device N across the second adhesive coating AC3 in the direction of the arrow. In the embodiment of FIG. 6, the elongate device N extends along an axis AN and the transducer laminate TL has a substantially rectangular outline; and the wrapping is performed by arranging a long edge RE of the rectangle at an acute angle α to the axis AN of the elongate device N prior to rolling the elongate device N across the second adhesive coating AC3. Thereby a simplified spiral winding assembly process is provided.

Figures 7, 8A, 8B:
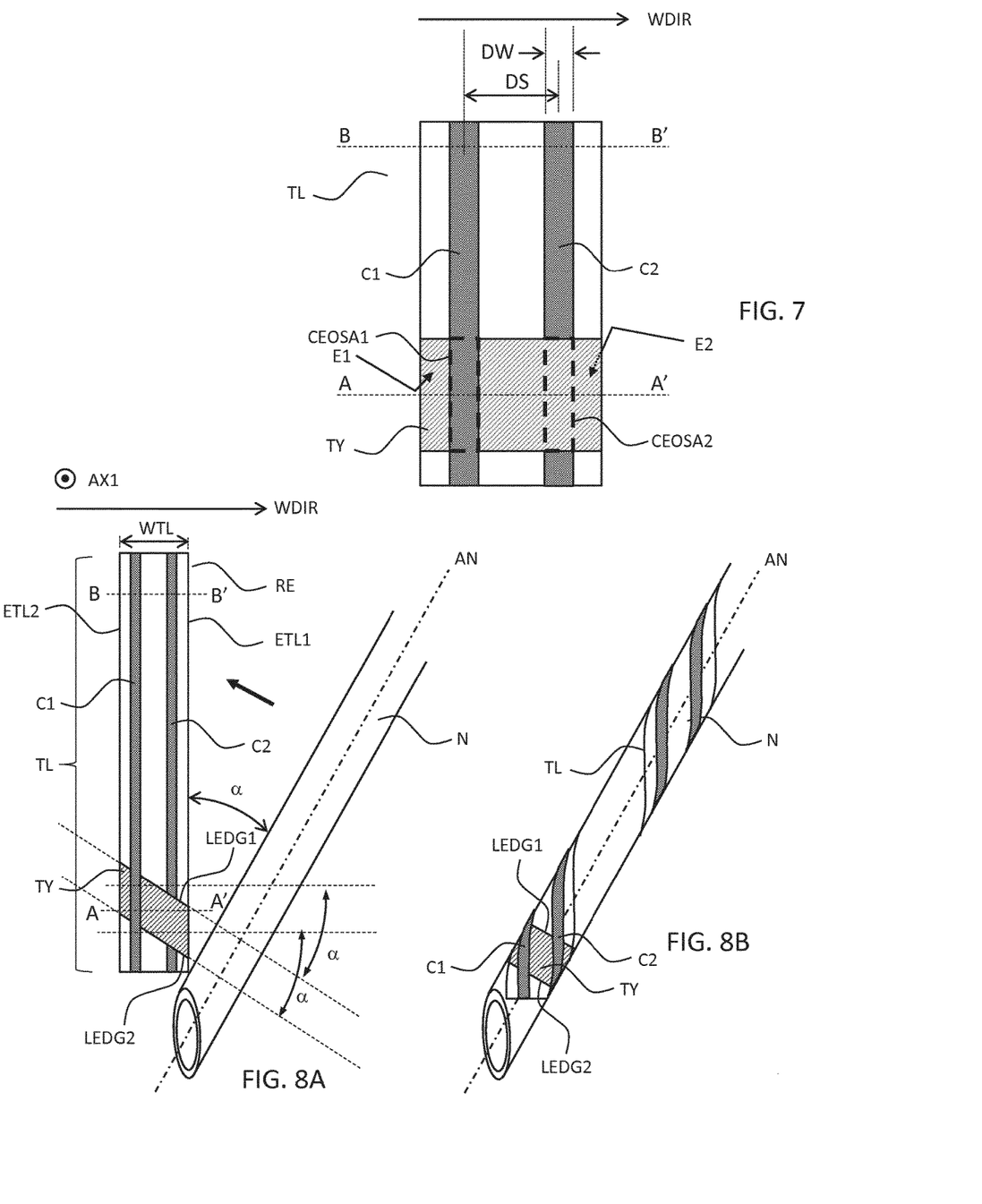
FIG. 7 illustrates a planar view of a transducer laminate TL in accordance with some aspects of the invention in which each of the two electrical conductors C1, C2 overlaps with its corresponding electrode E1, E2 to define a conductor-to-electrode overlap surface area CEOSA1, CEOSA2.
FIGS. 8A and 8B illustrate some aspects of the invention, particularly in FIG. 8A, a transducer laminate TL and a separate elongate device N, the transducer laminate TL having a pair of substantially parallel layer edges LEDG1, LEDG2 that are arranged at an acute angle α to the transducer laminate width direction WDIR, and in FIG. 8B, a transducer laminate TL that is wrapped around the elongate device N in a spiral.

FIG. 7 illustrates a planar view of a transducer laminate TL in accordance with some aspects of the invention in which each of the two electrical conductors C1, C2 overlaps with its corresponding electrode E1, E2 to define a conductor-to-electrode overlap surface area CEOSA1, CEOSA2. In the illustration, electrode E1 overlaps with and is disposed on top of transducer layer TY, and electrode E2 overlaps with and is disposed below transducer layer TY. Each overlap is at the first position A-A' and is in a plane that is coincident with the respective electrode E1, E2. Preferably the ratio of the two conductor to electrode overlap surface areas, i.e. CEOSA1/CEOSA2 is in the range 0.9-1.1, and even more preferably this ratio can be made equal to unity. The overlap surface area determines a contact resistance between each conductor and its respective electrode. By making the two conductor to electrode overlap surface areas more or less equal, reflections of electrical signals back along the conductors can be controlled. The total impedance presented by the electrical circuit comprising the conductors, the electrodes, and the transducer is also affected to some extent by these respective surface areas. Thus improved control over this impedance is provided through the above ratio of the two conductor to electrode overlap surface areas.

FIGS. 8A and 8B illustrate some aspects of the invention, particularly in FIG. 8A a transducer laminate TL and a separate elongate device N, the transducer laminate TL having a pair of substantially parallel layer edges LEDG1, LEDG2 that are arranged at an acute angle α to the transducer laminate width direction WDIR, and in FIG. 8B a transducer laminate TL that is wrapped around the elongate device N in a spiral. Transducer laminate TL of FIG. 8A is suitable for attachment to an elongate device, such as the elongate device N having an axis AN that is also illustrated in FIG. 8A. As described elsewhere, the elongate device may be a device in general, or more specifically an interventional device such as a medical needle, a cannula, a catheter, a guidewire and the like. The transducer laminate TL may be attached to such an elongate device AN by wrapping the transducer laminate around the axis AN of the elongate device N in a spiral, in other words by rolling the elongate device N across the transducer laminate TL. Axis AN may be more specifically described as a longitudinal axis, or an axis of rotation. Returning to the transducer laminate TL of FIG. 8A, this has a transducer laminate width direction WDIR that is perpendicular to both the transducer axis AX1 and to the common direction along which the two electrical conductors C1, C2 extend. Transducer axis AX1 is illustrated as a dot within a circle in FIG. 8A to illustrate that this axis runs perpendicularly to the plane of the page of the illustration. Moreover, the transducer laminate has a pair of substantially parallel transducer laminate edges ETL1, ETL2, and the extent of the transducer laminate TL in the transducer laminate width direction WDIR is defined by the pair of substantially parallel transducer laminate edges ETL1, ETL2. At the first position A-A' along the length of the two electrical conductors C1, C2 the extent of the transducer layer TY and/or each of the electrodes E1, E2 along the common direction along which the two electrical conductors extend, is defined by a pair of substantially parallel layer edges LEDG1, LEDG2. Thus either the transducer layer, or its electrodes E1, E2, or both of these define layer edges LEDG1, LEDG2. Moreover each layer edge LEDG1, LEDG2 is arranged at an acute angle α to the transducer laminate width direction WDIR. As a consequence, when the transducer laminate TL is arranged so that one of the pair of transducer laminate edges ETL1, ETL2 forms the acute angle α to the axis AN of a separate elongate device N and the transducer laminate is subsequently wrapped around the axis AN of the elongate device N in a spiral, the pair of layer edges LEDG1, LEDG become arranged substantially perpendicularly to the axis AN of the elongate device N. This provides a transducer laminate with a transducer layer that can be more accurately positioned with respect to the axis of an elongate device. This is particularly suited to the position sensing application mentioned above in relation to PCT/IB2015/052425, in which the sensor is an ultrasound sensor and the position of the ultrasound sensor is indicative of the position of an elongate device in an ultrasound field. Since the sensor becomes, by virtue of the acute angle α, wrapped circumferentially about the axis of the elongate device in the form of a strip or a band that is arranged perpendicularly to the axis, its position is invariant along the axis as the elongate device is rotated. Thus the detected position of the sensor is independent of the rotation of the interventional device about its axis. By contrast, a sensor that is wrapped such that its extent-defining edges are wrapped as a spiral around the axis of the elongate device provides a device in which the position of a detected signal varies with rotation. Likewise when the transducer layer is a transducer in general, the above transducer layer arrangement provides that the position of the sensed signal, is invariant with rotational angle of the interventional device about its axis.

By an "acute" angle α in relation to the embodiment of FIG. 8 it is intended to mean that the angle exceeds zero degrees and is less than 90 degrees. The angle α that is used may depend on the angle at which the transducer layer is to be presented to the axis of the elongate device for wrapping. As such, angles in the range 5 degrees-85 degrees may be particularly beneficial.

Moreover, while the embodiment of FIGS. 8A and 8B has been described primarily in relation to the substantially parallel layer edges LEDG1, LEDG2 being edges of the transducer layer TY, edges LEDG1, LEDG2 may alternatively or additionally be edges of each of the electrodes E1, E2 (not shown in FIGS. 8A and 8B). In some transducer layers, particularly transducer layers with high surface resistance, the activity of the transducer layer is defined by the contact area of the electrodes. Thus, limiting the activity of the transducer via the electrodes may alternatively be used to ensure that the position of the transducer's sensed or emitted signal is, in the same way, invariant with rotation about the axis AN of the elongate device N.

The invention is exemplified by the following Examples:

Example 1

Transducer laminate TL comprising:
two adhesive-coated foils F1, F2, wherein each foil F1, F2 has an adhesive coating AC1, AC2 on one of its two surfaces;
two electrical conductors C1, C2 that are arranged alongside each other and which extend along a common direction; and
a transducer layer TY having an electrode E1, E2 on each of its two surfaces;
wherein the adhesive coatings AC1, AC2 of the two adhesive-coated foils F1, F2 face each other;
and wherein at a first position A-A' along the length of the two electrical conductors C1, C2 the two electrical conductors C1, C2 are sandwiched between the adhesive coatings AC1, AC2 of the two adhesive-coated foils, and the transducer layer TY is also sandwiched between the two electrical conductors C1, C2 such that one of the two electrical conductors makes electrical contact with one of the two electrodes E1, E2 of the transducer layer TY, and such that the other of the two electrical conductors C1, C2 makes electrical contact with the other of the two electrodes E1, E2 of the transducer layer TY;

and wherein at a second position B-B' along the length of the two electrical conductors C1, C2 the two electrical conductors C1, C2 are sandwiched between the adhesive coatings AC1, AC2 of the two adhesive-coated foils and there is no transducer layer TY sandwiched between the two electrical conductors C1, C2.

Example 2

Transducer laminate TL according to Example 1 wherein the two electrical conductors C1, C2 are laterally displaced with respect to the transducer layer TY such that there is a gap DS between the centers of the two electrical conductors C1, C2 in a plane parallel to the transducer layer.

Example 3

Transducer laminate TL according to Example 2 wherein each of the two electrical conductors C1, C2 comprises a wire having a substantially circular cross section.

Example 4

Transducer laminate TL according to Example 3 wherein each wire has a diameter DW; and wherein the ratio of the gap between the centers of the two electrical conductors to the wire diameter DS/DW is greater than or equal to 10.

Example 5

Transducer laminate TL according to any one of Examples 1-4 wherein each foil is formed from one of the following materials: Polyvinylidene fluoride, a PVDF co-polymer such as polyvinylidene fluoride trifluoroethylene, a PVDF ter-polymer such as P(VDF-TrFE-CTFE).

Example 6

Transducer laminate TL according to any one of Examples 1-4 wherein at least one of the two adhesive-coated foils F1, F2 of the transducer laminate TL is further provided with one or more openings for making electrical contact to at least a portion of each of the two electrical conductors C1, C2.

Example 7

Transducer laminate TL according to any previous Example wherein i) at least one of the foils is provided by a conductive material, and/or ii) at least one of the foils F1, F2 comprises a conductive layer CL that extends substantially along the length of the two electrical conductors C1, C2.

Example 8

Transducer laminate TL according to any previous Example wherein one of the two adhesive-coated foils F1, F2 further comprises a second adhesive coating AC3 on the other of its two surfaces.

Example 9

Transducer laminate TL according to any previous Example wherein at least one of the adhesive coatings AC1, AC2, AC3 is a pressure sensitive adhesive coating.

Example 10

Transducer laminate TL according to any previous Example wherein the transducer is an ultrasound transducer that is capable of emitting and/or detecting ultrasound signals.

Example 11

Medical device, for example a catheter or a needle or an ultrasound-based tracking system, comprising the transducer laminate TL of any previous Example.

Example 12

Method of assembling the transducer laminate TL of any one of Example 1-10 comprising the steps of:
providing two adhesive-coated foils F1, F2, wherein each foil F1, F2 has an adhesive coating AC1, AC2 on one of its two surfaces;
providing two electrical conductors C1, C2 that are arranged alongside each other and which extend along a common direction; and
providing a transducer layer TY having an electrode E1, E2 on each of its two surfaces;
arranging the two adhesive-coated foils F1, F2 such that the adhesive coatings AC1, AC2 of the two adhesive-coated foils F1, F2 face each other;
arranging the transducer layer TY between the two adhesive-coated foils F1, F2 at a first position A-A' along the length of the two electrical conductors C1, C2 such that the two electrical conductors C1, C2 are sandwiched between the adhesive coatings AC1, AC2 of the two adhesive-coated foils, and such that the transducer layer TY is also sandwiched between the two electrical conductors C1, C2 and such that one of the two electrical conductors makes electrical contact with one of the two electrodes E1, E2 of the transducer layer TY, and such that the other of the two electrical conductors C1, C2 makes electrical contact with the other of the two electrodes E1, E2 of the transducer layer TY;
arranging that, at a second position B-B' along the length of the two electrical conductors C1, C2 the two electrical conductors C1, C2 are sandwiched between the adhesive coatings AC1, AC2 of the two adhesive-coated foils, and that there is no transducer layer TY sandwiched between the two electrical conductors C1, C2.

Example 13

Method of attaching the transducer laminate TL of Example 8 to an elongate device N comprising the steps of:

attaching, via the second adhesive coating AC3, the transducer laminate TL of Example 7 to the elongate device N; and wrapping the Transducer laminate TL around the elongate device N in the form of a spiral.

Example 14

Method of Example 13 wherein the wrapping is performed by rolling the elongate device N across the second adhesive coating AC3.

Example 15

Method of Example 14 wherein the elongate device N extends along an axis AN and wherein the transducer laminate TL has a substantially rectangular outline; and wherein the wrapping is performed by arranging a long edge RE of the rectangle at an acute angle α to the axis AN of the elongate device N prior to rolling the elongate device N across the second adhesive coating AC3.

To summarize, a transducer laminate having electrical connectors which make contact with a transducer is disclosed herein. A simplified assembly having electrical connection with the transducer is thus provided.

Whilst the invention has been illustrated and described in detail in the drawings and foregoing description in relation to a medical needle, such illustrations and description are to be considered illustrative or exemplary and not restrictive; the invention is not limited to the disclosed embodiments and can be used for transferring transducers to articles in general.

The invention claimed is:

1. A transducer laminate comprising:
two adhesive-coated foils, wherein each foil has an adhesive coating on one of its two surfaces;
two electrical conductors that are arranged alongside each other and which extend along a common direction; and
a transducer layer having an electrode on each of its two surfaces; and wherein a minimum separation between the two electrodes defines a transducer axis;
wherein the adhesive coatings of the two adhesive-coated foils face each other;
and wherein at a first position along the length of the two electrical conductors the two electrical conductors are sandwiched between the adhesive coatings of the two adhesive-coated foils, and the transducer layer is also sandwiched between the two electrical conductors such that one of the two electrical conductors makes electrical contact with one of the two electrodes of the transducer layer, and such that the other of the two electrical conductors makes electrical contact with the other of the two electrodes of the transducer layer; the two adhesive-coated foils being arranged layer-wise along the transducer axis such that one of the two adhesive-coated foils is on one side of the transducer layer and the other of the two adhesive-coated foils is on the other side of the transducer layer;
and wherein at a second position along the length of the two electrical conductors the two electrical conductors are sandwiched between the adhesive coatings of the two adhesive-coated foils and there is no transducer layer sandwiched between the two electrical conductors.

2. The transducer laminate as claimed in claim 1, wherein at the first position each electrical conductor is further held in physical contact with its corresponding electrode by one of the two adhesive-coated foils and its adhesive coating.

3. The transducer laminate as claimed in claim 1, wherein at the first position the electrical contact between each electrical conductor and its corresponding electrode is provided without an electrically conductive adhesive or a solder.

4. The transducer laminate as claimed in claim 1, wherein each adhesive coating is formed from an electrically insulating material.

5. The transducer laminate as claimed in claim 1, wherein at the first position each electrode has an electrode lateral width in a transducer laminate width direction that is perpendicular to both the transducer axis and to the common direction along which the two electrical conductors extend; and wherein each adhesive-coated foil has a foil lateral width in the transducer laminate width direction; the foil lateral width being greater than or equal to the electrode lateral width.

6. The transducer laminate as claimed in claim 5, wherein at the first position each of the two electrical conductors overlaps with its corresponding electrode to define a conductor-to-electrode overlap surface area in a plane that is coincident with the respective electrode;
and wherein the ratio of the two conductor to electrode overlap surface areas is in the range 0.9-1.1.

7. The transducer laminate as claimed in claim 6, for attachment to an elongate device having an axis;
wherein the transducer laminate has a transducer laminate width direction that is perpendicular to both the transducer axis and to the common direction along which the two electrical conductors extend, and a pair of substantially parallel transducer laminate edges, and wherein the extent of the transducer laminate in the transducer laminate width direction is defined by the pair of substantially parallel transducer laminate edges;
wherein at the first position along the length of the two electrical conductors the extent of the transducer layer and/or each of the electrodes along the common direction along which the two electrical conductors extend, is defined by a pair of substantially parallel layer edges, each layer edge being arranged at an acute angle (α) to the transducer laminate width direction; such that when the transducer laminate is arranged so that one of the pair of transducer laminate edges forms the acute angle (α) to the axis of the elongate device and is subsequently wrapped around the axis of the elongate device in a spiral, the pair of layer edges are substantially perpendicular to the axis of the elongate device.

8. The transducer laminate as claimed in claim 1, wherein the two electrical conductors are laterally displaced with respect to the transducer layer such that there is a gap between the centers of the two electrical conductors in a plane parallel to the transducer layer.

9. The transducer laminate as claimed in claim 8, wherein each of the two electrical conductors comprises a wire having a substantially circular cross section.

10. The transducer laminate as claimed in claim 9, wherein each wire has a diameter; and wherein the ratio of the gap between the centers of the two electrical conductors to the wire diameter is greater than or equal to 10.

11. The transducer laminate as claimed in claim 1, wherein each foil is formed from one of the following materials: Polyvinylidene fluoride, a PVDF co-polymer such as polyvinylidene fluoride trifluoroethylene, a PVDF ter-polymer such as P(VDF-TrFE-CTFE).

12. The transducer laminate as claimed in claim 1, wherein at least one of the two adhesive-coated foils of the transducer laminate is further provided with one or more openings for making electrical contact to at least a portion of each of the two electrical conductors.

13. The transducer laminate as claimed in claim 1, wherein i) at least one of the foils is provided by a conductive material, and/or ii) at least one of the foils comprises a conductive layer that extends substantially along the length of the two electrical conductors.

14. The transducer laminate as claimed in claim 13, wherein one of the two adhesive-coated foils further comprises a second adhesive coating on the other of its two surfaces.

15. The transducer laminate as claimed in claim 14, wherein at least one of the adhesive coatings is a pressure sensitive adhesive coating.

16. The transducer laminate as claimed in claim 15, wherein the transducer is an ultrasound transducer that is capable of emitting and/or detecting ultrasound signals.

17. A medical device, for example a catheter or a needle or an ultrasound-based tracking system, comprising the transducer laminate of claim 1.

18. A method of assembling the transducer laminate of claim 1 comprising the steps of:
   providing two adhesive-coated foils, wherein each foil has an adhesive coating on one of its two surfaces;
   providing two electrical conductors that are arranged alongside each other and which extend along a common direction; and
   providing a transducer layer having an electrode on each of its two surfaces; and wherein a minimum separation between the two electrodes defines a transducer axis;
   arranging the two adhesive-coated foils such that the adhesive coatings of the two adhesive-coated foils face each other;
   arranging the transducer layer between the two adhesive-coated foils at a first position along the length of the two electrical conductors such that the two electrical conductors are sandwiched between the adhesive coatings of the two adhesive-coated foils, and such that the transducer layer is also sandwiched between the two electrical conductors and such that one of the two electrical conductors makes electrical contact with one of the two electrodes of the transducer layer, and such that the other of the two electrical conductors makes electrical contact with the other of the two electrodes of the transducer layer; the two adhesive-coated foils being arranged layer-wise along the transducer axis such that one of the two adhesive-coated foils is on one side of the transducer layer and the other of the two adhesive-coated foils is on the other side of the transducer layer;
   arranging that, at a second position along the length of the two electrical conductors the two electrical conductors are sandwiched between the adhesive coatings of the two adhesive-coated foils, and that there is no transducer layer sandwiched between the two electrical conductors.

19. The method of attaching the transducer laminate as claimed in claim 14, to an elongate device, comprising the steps of:
   attaching, via the second adhesive coating, the transducer laminate to the elongate device; and
   wrapping the Transducer laminate around the elongate device in the form of a spiral.

20. The method as claimed in claim 19, wherein the wrapping is performed by rolling the elongate device across the second adhesive coating.

21. The method as claimed in claim 20, wherein the elongate device extends along an axis and wherein the transducer laminate has a substantially rectangular outline; and wherein the wrapping is performed by arranging a long edge of the rectangle at an acute angle ($\alpha$) to the axis of the elongate device prior to rolling the elongate device across the second adhesive coating.

* * * * *